(12) United States Patent
Soppimath et al.

(10) Patent No.: US 12,194,141 B2
(45) Date of Patent: *Jan. 14, 2025

(54) SUCCINYLCHOLINE PREFILLED SYRINGE, COMPOSITIONS AND METHODS

(71) Applicant: Nevakar Injectables Inc., Bridgewater, NJ (US)

(72) Inventors: Kumaresh Soppimath, Skillman, NJ (US); Tushar Hingorani, Bridgewater, NJ (US); Anant Patel, Pompton Lakes, NJ (US)

(73) Assignee: NEVAKAR INJECTABLES INC., Bridgewater, NJ (US)

( * ) Notice: Subject to any disclaimer, the term of this patent is extended or adjusted under 35 U.S.C. 154(b) by 1028 days.

This patent is subject to a terminal disclaimer.

(21) Appl. No.: 17/142,744

(22) Filed: Jan. 6, 2021

(65) Prior Publication Data
US 2021/0121395 A1  Apr. 29, 2021

Related U.S. Application Data

(60) Continuation-in-part of application No. 16/909,340, filed on Jun. 23, 2020, now Pat. No. 11,779,535, (Continued)

(51) Int. Cl.
*A61K 9/00* (2006.01)
*A61K 31/137* (2006.01)
(Continued)

(52) U.S. Cl.
CPC .......... *A61K 9/0019* (2013.01); *A61K 31/137* (2013.01); *A61K 31/225* (2013.01); (Continued)

(58) Field of Classification Search
CPC ........ A61K 31/37; A61K 47/12; A61K 47/02; A61M 39/10; A61M 5/178
See application file for complete search history.

(56) References Cited

U.S. PATENT DOCUMENTS 9,205,243 B2   12/2015   Lopez et al.
9,750,926 B2   9/2017   Lopez et al.
(Continued)

FOREIGN PATENT DOCUMENTS

WO   2017220553 A1   12/2017

OTHER PUBLICATIONS

Hospira, Inc. "Quelicin, Succinylcholine Chloride Injection, USP" Sep. 2010; 9 pgs (Year: 2010).*

(Continued)

*Primary Examiner* — Chelsea E Stinson
*Assistant Examiner* — Anh Bui
(74) *Attorney, Agent, or Firm* — ArentFox Schiff LLP & Endo (57) ABSTRACT

Pre-filled syringes, pharmaceutical compositions, and kits and methods relating to same allow for emergency administration of one or more drugs from prefilled glass syringes to a patient via a needleless connector. In preferred embodiments, the prefilled glass syringe has a drug volume of at least 5 mL, has a Luer-lock, and has a syringe tip with an internal channel that has a diameter of about 1.7 mm. Such syringes advantageously allow storage of emergency drugs without leaching of plastic materials and degradation, and substantially improve the safety profile where the syringe is attached to an IV line via a needleless connector.

14 Claims, 6 Drawing Sheets

Related U.S. Application Data which is a division of application No. 16/836,152, filed on Mar. 31, 2020, now Pat. No. 10,722,453, which is a division of application No. 16/272,815, filed on Feb. 11, 2019, now Pat. No. 10,682,308.

(60) Provisional application No. 62/642,326, filed on Mar. 13, 2018.

(51) Int. Cl.

| | | |
|---|---|---|
| *A61K 31/225* | (2006.01) | |
| *A61K 47/02* | (2006.01) | |
| *A61K 47/12* | (2006.01) | |
| *A61M 5/145* | (2006.01) | |
| *A61M 5/178* | (2006.01) | |
| *A61M 5/31* | (2006.01) | |
| *A61M 25/00* | (2006.01) | |
| *A61M 39/10* | (2006.01) | |

(52) U.S. Cl.
CPC .............. *A61K 47/02* (2013.01); *A61K 47/12* (2013.01); *A61M 5/1452* (2013.01); *A61M 5/178* (2013.01); *A61M 5/3129* (2013.01); *A61M 25/0097* (2013.01); *A61M 39/10* (2013.01)

(56) References Cited

U.S. PATENT DOCUMENTS

| | | | | |
|---|---|---|---|---|
| 2011/0130717 A1* | 6/2011 | David | ................. | A61M 5/3134 |
| | | | | 604/68 |
| 2012/0029438 A1* | 2/2012 | Vernizeau | ........... | A61M 5/3134 |
| | | | | 604/189 |
| 2013/0338602 A1 | 12/2013 | Thorley et al. | | |
| 2016/0022912 A1 | 1/2016 | Hernandez | | |
| 2016/0136352 A1* | 5/2016 | Smith | ................... | A61M 5/008 |
| | | | | 206/366 |
| 2018/0099137 A1 | 4/2018 | Fangrow | | |
| 2019/0001114 A1 | 1/2019 | Fangrow | | |
| 2019/0201630 A1 | 7/2019 | Vogt | | |

OTHER PUBLICATIONS

"FDA Drug Safety Communication: Connection problems involving certain needleless pre-filled glass syringes containing adenosine and amiodarone," Drug Safety and Availability, May 6, 2011; 5 pgs. Retrieved from https://www.fda.gov/Drugs/DrugSafety/ucm254215.

"One-Link Needle-free IV Connector," Sales Brochure, Baxter Healthcare Corporation, Nov. 2013; 6 pgs.

Ethiopian Food, Medicine and Health Care Administration and Control Authority, "Emergency Medicines List (EML), First Edition," Nov. 2014, Addis Ababa; 41 pgs.

Excerpt from US FDA Jan. to Jun. 2019 outsourcing facility product report; 1 pg.

Excerpt from US FDA Jul. to Dec. 2018 outsourcing facility product report; 1 pg.

Hadaway, Lynn, MEd, RNC, CRNI, "Needleless Connectors for IV Catheters," AJN, Nov. 2012, 112(11):32-44.

Hospira, Inc. "Quelicin, Succinylcholine Chloride Injection, USP" Sep. 2010; 9 pgs.

Intermountain Healthcare, "Giving Medication: IV Push" 2014, 2 pgs.

\* cited by examiner

SUCCINYLCHOLINE PREFILLED SYRINGE, COMPOSITIONS AND METHODS

This application is a continuation-in-part application of US patent application with the Ser. No. 16/909,340, which was filed Jun. 23, 2020, which claims priority to U.S. Pat. No. 10,722,453, which was filed Mar. 31, 2020, which claims priority to U.S. Pat. No. 10,682,308, which was filed Feb. 11, 2019, and which claims priority to US provisional patent application with the Ser. No. 62/642,326, which was filed Mar. 13, 2018, the contents of which are herein incorporated by reference.

FIELD OF THE INVENTION

The present disclosure relates to kits, prefilled syringes, pharmaceutical compositions and methods of use thereof, particularly as it relates to prefilled glass syringes containing emergency medication for administration through needleless connectors.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Needleless devices for connecting intravenous (IV) catheters, administration sets, and syringes have been developed over the last decades and helped significantly reduce needlestick injuries among health care providers. Unfortunately, the use of needleless connectors has also been associated with an increase in various complications such as catheter-related bloodstream infection and catheter lumen occlusion. To circumvent at least some of these problems, various improvements have been implemented. For example, several simple needleless connectors use a split septum and/or other non-moving parts to avoid backflow of blood into the IV line while still allowing needleless access to the IV line. More complex needleless connectors employ internal moving components such as unidirectional valves to control the flow of fluids within the connector. While simple connectors advantageously provide simplicity of use and manufacture, negative fluid displacement or reflux will often occur upon withdrawal of the cannula due to their relatively large size. On the other hand, connectors with mechanical valves are more complex and therefore less simple in manufacture, but typically have no or only minor reflux.

Figure 1:
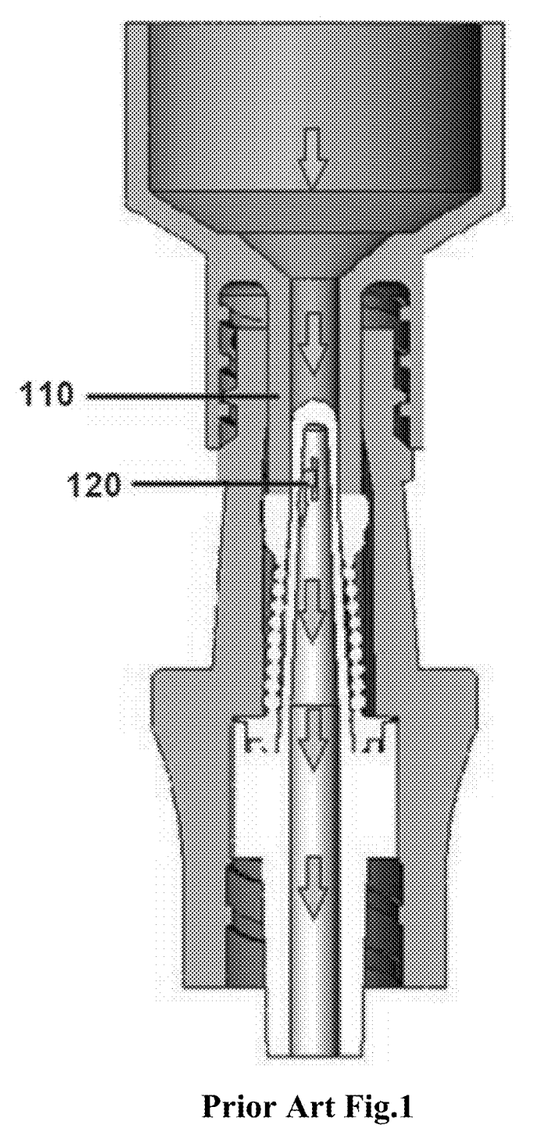
FIG. 1 depicts a cross sectional view of an exemplary known needleless connector with a reversed internal blunt cannula attached to a syringe with a male luer tip.

A representative complex needleless connector is shown in Prior Art FIG. 1, in which a syringe with a male luer tip 110 is coupled to a needleless connector with a reversed internal blunt cannula 120. Exemplary complex needleless connectors are described, for example, in U.S. Pat. Nos. 9,205,243 and 9,750,926, and such and similar connectors may further include a sealing member and regulator acting as a second valve as is described, for example, in US Publication Nos. 20180099137 and 20190001114. While such and other complex needleless connectors eliminate the risk of needlestick injuries and at least conceptually simplify operation, catheter related blood stream infections have become more prevalent.

Figure 2A:
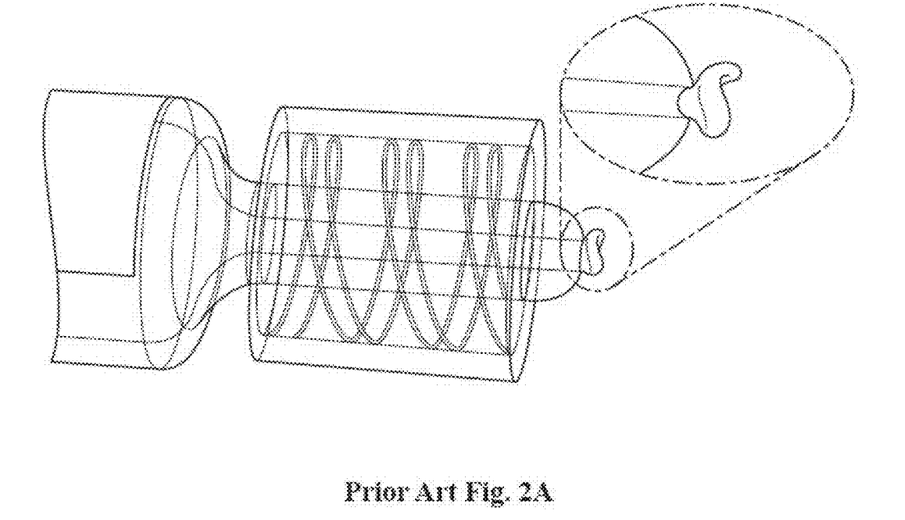
FIG. 2A depicts a damaged/clogged syringe tip after disconnection from a needleless connector with a reversed internal blunt cannula, and Prior Art
Figure 2B:
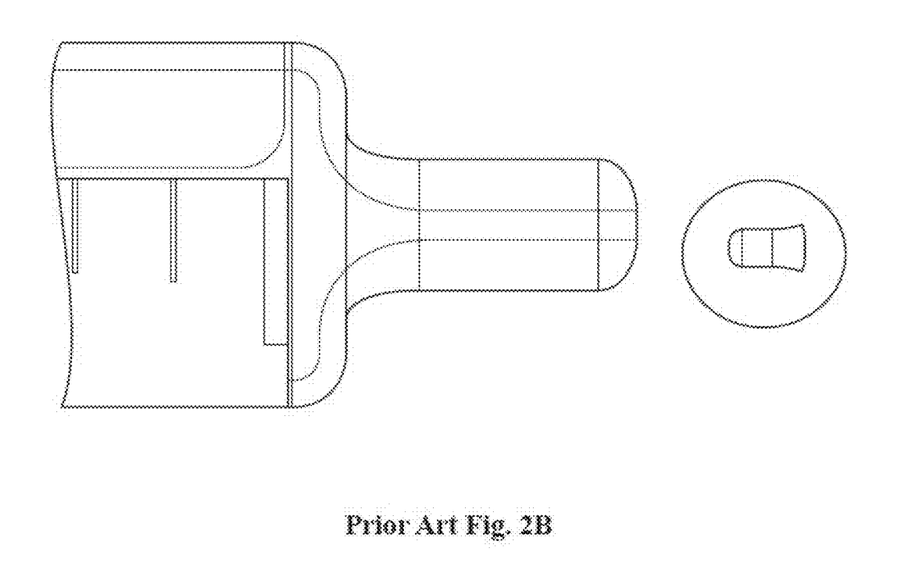
FIG. 2B depicts a glass syringe tip and broken off tip of a reversed internal blunt cannula of a needleless connector.

Worse yet, and particularly in emergency settings where certain drugs (e.g., adenosine, amiodarone, succinylcholine, etc.) need to be administered without delay and interruption, complex needleless connectors can contribute to catastrophic failure. In a Drug Safety Communication, the FDA had more recently indicated that pre-filled glass syringes can become clogged and malfunction during the process of connecting them to pin-activated needleless IV access systems (see Prior Art FIGS. 2A and 2B). Unfortunately, such failure is not detected until after the syringe is inserted into the pin-activated needleless i.v. access system. For example, the action of inserting the syringe can cause the pin in the access system to clog or break off in the syringe tip, thus preventing delivery of the medication and necessitating placement of a new i.v. access line. As a consequence, the FDA advised that the use of needleless pre-filled glass syringes in emergency situations should be avoided, if possible (see URL: www.fda.gov/Drugs/DrugSafety/ucm254215.htm). Moreover, because of recent adverse glass syringe connection events, the FDA has recognized that demonstrating conformity to the ISO 11040-4 standard alone does not ensure that the glass syringes can be properly connected to connecting devices. Therefore, sponsors who seek to rely on conformity to the ISO 11040-4 standard in submissions for glass syringe products should also submit information from supplemental tests to demonstrate that the glass syringe can be properly connected to connecting devices. Such safe connection has been elusive and challenging, particularly for prefilled glass syringes.

Thus, even though various methods of delivering emergency medication from syringes via needleless connectors are known in the art, all or almost all of them suffer from various disadvantages. Consequently, there is a need to provide improved devices, kits, and methods using glass syringes that improve safety and reliability of drug administration in emergency settings.

SUMMARY OF THE INVENTION

Various devices, compositions, kits, and methods are presented in which problems associated with emergency IV administration of various drug compositions via needleless connectors can be avoided. In especially preferred aspects, the emergency drug composition comprises succinylcholine that is contained in a prefilled glass syringe, and the syringe has a Luer-lock and a syringe tip with an internal channel that has a diameter of about 1.7 mm.

In one aspect of the inventive subject matter, the inventors contemplate a method for intravenously administering succinylcholine to a patient and/or providing skeletal muscle relaxation to a patient in need thereof that includes the steps of (a) providing a prefilled glass syringe containing a succinylcholine composition, wherein the succinylcholine composition comprises succinylcholine chloride, sodium chloride, and water, wherein the succinylcholine composition is substantially free of preservatives, and wherein the succinylcholine composition has a pH of about 3.0 to about 4.5, and wherein the syringe has a Luer-lock and a syringe tip with an internal channel that has a diameter of about 1.7 mm; (b) reversibly attaching the syringe to a patient's intravenous line via the Luer-lock; (c) delivering the succinylcholine composition from the syringe into the patient's intravenous line; and (d) administering the succinylcholine composition from the patient's intravenous line to the patient.

In some embodiments, the step of reversibly attaching the syringe to a patient's intravenous line comprises attaching the syringe to a needleless connector, which may include a reversed internal blunt cannula. Most typically, but not necessarily, the glass syringe has a volume of at least 5 mL.

In other embodiments, the succinylcholine composition has an osmolality of about 260 to about 340 mOsm/kg, and/or the succinylcholine chloride is present in the succinylcholine composition in an amount of about 20 mg/mL and the sodium chloride is present in the succinylcholine composition in an amount of about 6 mg/mL. It is further contemplated that the succinylcholine composition further comprises a pH adjusting agent (e.g., hydrochloric acid and/or sodium hydroxide), and/or that the pH of the succinylcholine composition is about 3.6.

With respect to the syringe it is contemplated that the syringe has a glide force of about 1 to about 20 N, and/or that the syringe has a break loose force of about 10 to about 30 N. In further embodiments, the syringe contains about 5 mL or about 10 mL of the succinylcholine composition, which may be administered to the patient at a rate of about 0.5 to about 10 mg per minute. Preferably, the succinylcholine composition in the glass syringe contains not more than about 6% total impurities after storage at 2-8° C. for 15 months as determined by HPLC. Viewed from a different perspective, the succinylcholine composition disposed in the glass syringe contains not more than about 4% succinylmonocholine chloride after storage at 2-8° C. for 15 months as determined by HPLC, and/or the succinylcholine composition disposed in the glass syringe contains not more than about 1% succinic acid after storage at 2-8° C. for 15 months as determined by HPLC.

In another aspect of the inventive subject matter, the inventors contemplate a kit that comprises a prefilled glass syringe containing a succinylcholine composition, wherein the succinylcholine composition comprises succinylcholine chloride, sodium chloride, and water, wherein the succinylcholine composition is substantially free of preservatives, and wherein the succinylcholine composition has a pH of about 3.0 to about 4.5. Preferably, the syringe has a Luer-lock and a syringe tip with an internal channel that has a diameter of about 1.7 mm.

Most typically, the glass syringe has a volume of at least 5 ml. Contemplated kits may further include an IV administration set with at least one needleless connector (e.g., needleless connector with a reversed internal blunt cannula).

With respect to contemplated succinylcholine compositions it is typically preferred that the succinylcholine composition has an osmolality of about 260 to about 340 mOsm/kg, and/or that the succinylcholine chloride is present in the succinylcholine composition in an amount of about 20 mg/mL and the sodium chloride is present in the succinylcholine composition in an amount of about 6 mg/mL. Moreover it is contemplated that the succinylcholine composition further comprises a pH adjusting agent (e.g., hydrochloric acid and/or sodium hydroxide) and that the pH of the succinylcholine composition is about 3.6. In some embodiments, the succinylcholine composition disposed in the glass syringe contains not more than about 6% total impurities after storage at 2-8° C. for 15 months as determined by HPLC, and in other embodiments the succinylcholine composition disposed in the glass syringe contains not more than about 4% succinylmonocholine chloride after storage at 2-8° C. for 15 months as determined by HPLC. In further embodiments, the succinylcholine composition disposed in the glass syringe contains not more than about 1% succinic acid after storage at 2-8° C. for 15 months as determined by HPLC.

Therefore, viewed from a different perspective, the inventors also contemplate a kit that comprises a prefilled glass syringe containing a drug for emergency medical administration, wherein the glass syringe has a volume of at least 5 ml, wherein the glass syringe has a luer-lock and a syringe tip with an internal channel that has a diameter of about 1.7 mm, and wherein the glass syringe and the drug are sterilized.

In particularly preferred aspects, the drug is succinylcholine, ephedrine, amiodarone, adenosine, epinephrine, atropine, methylprednisolone, metoprolol, diltiazem, or procainamide, and contemplated kits may further include an IV administration set with at least one needleless connector, and particularly a needleless connector with a reversed internal blunt cannula.

Viewed from yet another perspective, the inventors contemplate a prefilled glass syringe containing a drug composition for emergency medical administration of the drug through a needleless connector, wherein the glass syringe has a volume of at least 5 ml, wherein the glass syringe has a luer-lock, and wherein the glass syringe has a syringe tip with an internal channel that has a diameter of about 1.7 mm.

For example, suitable drug compositions include succinylcholine, ephedrine, amiodarone, adenosine, epinephrine, atropine, methylprednisolone, metoprolol, diltiazem, and procainamide. For example, the drug composition may comprise succinylcholine chloride, sodium chloride, and water, wherein the succinylcholine composition is substantially free of preservatives, and wherein the succinylcholine composition has a pH of about 3.0 to about 4.5.

In still further aspects of the inventive subject matter, the inventors contemplate a prefilled syringe that comprises a syringe barrel containing a ready-to-administer medication, wherein the barrel is fluidly coupled to a syringe tip. A luer-lock is coupled to the syringe to allow reversible attachment of the syringe to a needleless connector having a reversed internal blunt cannula, wherein the luer lock comprises a luer collar that is rotatable about the syringe tip. A tip cap is further rotatably coupled to and removable from the luer collar, and a polymeric band is coupled to the syringe to prevent rotation of the luer collar about the syringe tip when the tip cap is removed for the luer collar.

In some embodiments, the polymeric band directly couples the syringe barrel to the luer collar, while in other embodiments the polymeric band indirectly couples the syringe barrel to the luer collar via a restraint ring (which may have first and second portions that can be moved relative to each other). While not limiting to the inventive subject matter it is preferred that the polymeric band comprises a shrink wrap polymer and/or an adhesive.

In further embodiments, the syringe is a glass syringe that may have a syringe tip having in internal channel with a diameter of between 1.2-2.2 mm (e.g., diameter of at least 1.5 mm or a diameter of about 1.7 mm). Most typically, the medication in the syringe is an emergency medication such as succinylcholine, ephedrine, amiodarone, adenosine, epinephrine, atropine, methylprednisolone, metoprolol, diltiazem, or procainamide. For example, where the emergency medication is a succinylcholine composition, the succinylcholine composition may have a pH of about 3.0 to about 4.5. Moreover, it is preferred that the succinylcholine composition, when disposed in a glass syringe, contains not more than about 6% total impurities after storage at 2-8° C.

for 15 months, followed by storage at about 25° C. for 14 days as determined by HPLC.

Therefore, viewed from a different perspective, the inventors also contemplate a prefilled glass syringe that comprises a glass syringe with a barrel that contains a ready-to-administer medication, wherein the barrel is fluidly coupled to a syringe tip. A luer-lock is coupled to the syringe to allow reversible attachment of the syringe to a needleless connector having a reversed internal blunt cannula, wherein the luer lock comprises a luer collar that is rotatable about the syringe tip. A tip cap is rotatably coupled to and removable from the luer collar, and a polymeric band is coupled to the syringe to prevent rotation of the luer collar about the syringe tip when the tip cap is removed for the luer collar. Preferably, the syringe tip has an internal channel that has a diameter of 1.2-2.2 mm inner diameter, wherein the diameter of the internal channel and/or a length of the syringe tip is configured such that the syringe tip can be inserted into the needleless connector at an angle with respect to a hypothetical central axis extending through the barrel and the tip of the syringe and a hypothetical central axis longitudinally extending through the needleless connector without the reversed internal blunt cannula contacting the inner surface of the tip. Most typically, the ready-to-administer medication is an emergency medication.

In some embodiments, the internal channel has a diameter of about 1.7 mm, and wherein the prefilled glass syringe contains 5 mL or 10 mL of the emergency medication. For example, suitable emergency medications include succinylcholine, ephedrine, amiodarone, adenosine, epinephrine, atropine, methylprednisolone, metoprolol, diltiazem, and procainamide. Where the emergency medication is succinylcholine and contains not more than about 6% total impurities after storage at 2-8° C. for 12 months, followed by storage at about 25° C. for 14 days as determined by HPLC. Most typically, the pH of a succinylcholine composition will be between about pH 3-4.

Various objects, features, aspects, and advantages will become more apparent from the following detailed description of preferred embodiments, along with the accompanying drawing in which like numerals represent like components.

BRIEF DESCRIPTION OF THE DRAWING

Prior Art

Prior Art

DETAILED DESCRIPTION

The inventors have now discovered that various emergency medications can be rapidly and safely administered through a needleless connector (that is typically fluidly coupled to an IV line into a patient) without the attendant risk of clogging or breakage that has been encountered in the past. More particularly, the inventors discovered that the likelihood of breakage can be significantly reduced by using a syringe having a widened inner diameter of a syringe tip. Advantageously, the inventors observed that such a widened inner diameter substantially increased the tolerance of the tip to angled insertion into a needleless connector and so dramatically decreased the likelihood of damaging static or moving internals of the needleless connector. Moreover, the inventors observed that such widening did not cause significant mechanical weakening of the syringe tip that could otherwise lead to chipping or breaking of the tip where a glass syringe is used.

Figure 3:
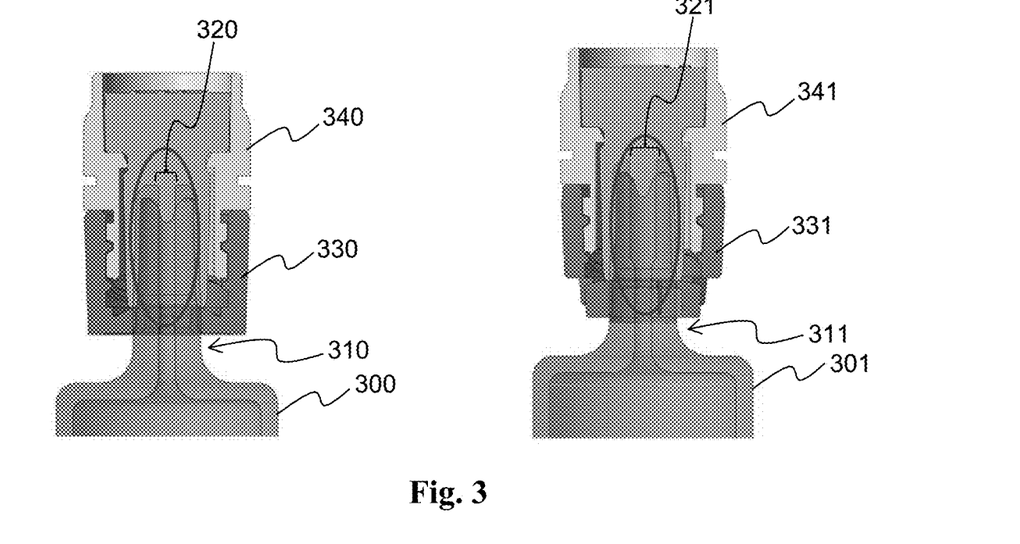
FIG. 3 depicts a comparison between a conventional attachment of a glass syringe to a needleless connector (left) and an attachment of a wide mouth glass syringe to a needleless connector (right) according to the inventive subject matter.
Figure 4:
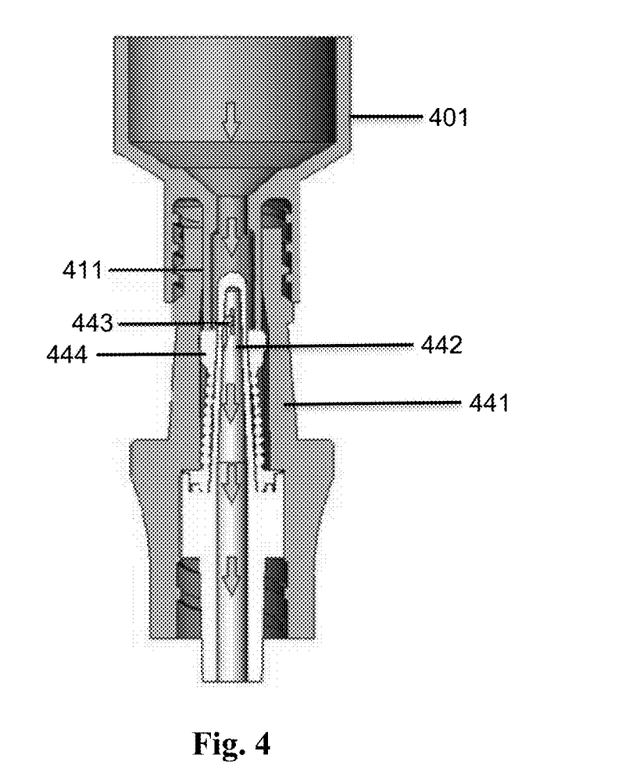
FIG. 4 depicts an exemplary connection between a syringe according to the inventive subject matter to a needleless connector with a reversed internal blunt cannula.
Figure 5A:
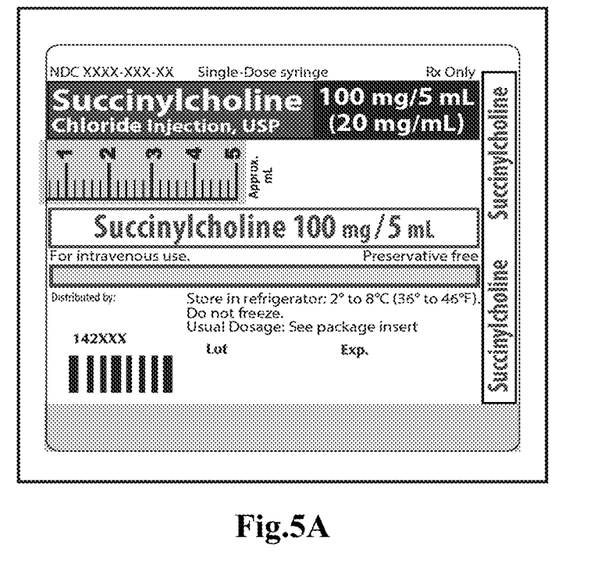
FIGS. 5A and 5B depict exemplary labels for prefilled syringes.
Figure 5B:
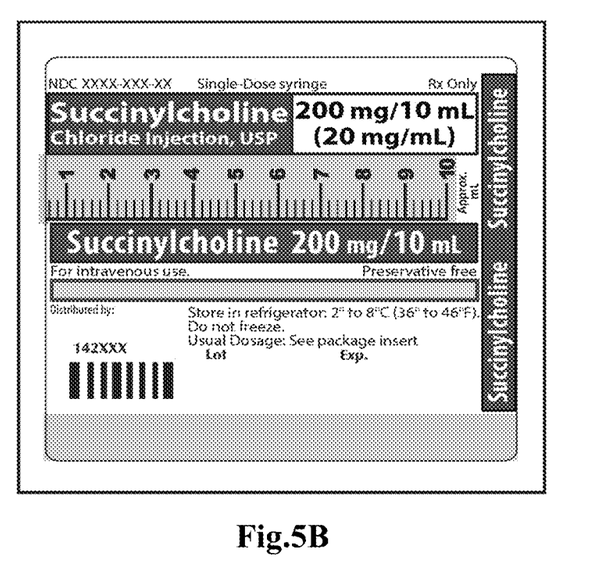

For example, FIG. 3 exemplarily depicts on the left hand a conventional syringe 300 that has a syringe tip 310 having an internal diameter 320 (here: 1.1 mm). The syringe also includes a luer lock connector 330 that is releasably coupled to matching luer lock of a needleless connector 340 (internals not shown) of an IV line. In contrast, on the right hand syringe 301 is shown having a syringe tip 311 with a significantly larger internal diameter 321 (here: 1.7 mm). The syringe also includes a luer lock connector 331 that is releasably coupled to matching luer lock of a needleless connector 341 (internals not shown) of an IV line. As should be readily apparent, the wider internal diameter accommodates angled insertion of the syringe tip 311 without jamming or breaking the internals (such as a reversed internal blunt cannula). FIG. 4 schematically illustrates one such embodiment in which syringe 401 has a syringe tip 411 with a significantly larger internal diameter. As can be seen, the reversed internal blunt cannula 442 of needleless connector 441 does not contact the internal walls of syringe tip 411. Instead, due to the wider inner diameter of the tip, an annular void space between the outer surface of the reversed internal blunt cannula and the internal walls of syringe tip is present that reduces or even entirely eliminates the risk of breakage or jamming of the front end of the reversed internal blunt cannula. FIGS. 5A and 5B depict exemplary labels for prefilled syringes according to the inventive subject matter.

Notably, despite the loss of a sealing surface (i.e., the outside surface of reversed internal blunt cannula against internal wall of the syringe tip) the connection between the syringe and the needleless connector nevertheless remained fluidly sealed by compression of elastic member 444 against the front end of the syringe tip and further by sealing engagement between the outer surface of the syringe tip 411 and the inner surface of the front portion of the connector that receives the syringe tip 411. Even at elevated pressure, these remaining surfaces maintained a fluid-tight contact that allowed rapid delivery of fluids through the connection.

Most preferably, the syringe for use in conjunction with the teachings herein may be a glass syringe (e.g., borosilicate glass), and in less preferred embodiments also a syringe manufactured from a polymeric material such as polypropylene or polyethylene. Moreover, it is preferred that the syringe has a volume of at least 5 mL or at least 10 mL, however, smaller volumes are also expressly contemplated. In one embodiment, the syringe has a volume of 5 mL. In another embodiment, the syringe has a volume of 10 mL. With respect to the tip it typically preferred that the tip is a centrally located tip, but eccentric tips are also deemed suitable. Most typically, the syringe tip will have an outer diameter, angle, and length that accommodate standard hub dimensions of luer lock needles and other luer lock equipment. Standards for luer lock connections are described in ISO 80369 and in DIN and EN standard 1707:1996 and 20594-1:1993, incorporated by reference herein.

For example, a typical tip of a syringe for luer-type connection will have a cone shaped configuration acting as the male portion of the luer lock with an overall length of about 7.5 mm from proximal to distal end (with respect to the barrel) of the tip, the proximal end of the tip having an outer diameter of about 4.45 mm and the distal end of the tip having an outer diameter of about 4.00 mm. Thus, a taper angle (relative to a hypothetical axis running through the center of the barrel and tip) of the tip walls between 0.5 degree and 5.0 degree are generally deemed suitable. However, the actual taper angle will in most cases correspond to the female luer lock counterpart such that the outer surface of the male and inner surface of the female connector will sealingly coupled the male and female portions (i.e., have the same angle along at least 70% of the length of the male tip).

With respect to the overall length of the tip as measured from proximal to distal end it is generally preferred that the length will be between about 8.5 mm to about 6.0 mm, however, various longer and shorter lengths are also deemed suitable for use herein. For example, suitable lengths include those between 5.5 mm and 7.0 mm, and between 6.0 mm and 8.0 mm, and between 7.0 mm and 9.0 mm. However, lengths of equal or less than 8.0 mm are generally preferred. With respect to the inner diameter of the tip it is generally preferred that the inner diameter is constant from the proximal to the distal end of the tip. Most typically the inner diameter will be about 1.7 mm, however various other inner diameters are also deemed suitable for use herein. For example, alternative inner diameters will generally be greater than 1.1 mm, or greater than 1.3 mm, or greater than 1.5 mm, or greater than 1.7 mm, or greater than 1.9 mm, or even greater. Thus, suitable inner diameters will be between 1.2-2.2 mm, or between 1.4-2.0 mm, or between 1.6-1.8 mm, or between 1.3-1.6 mm, or between 1.5-1.9 mm, or between 1.6-2.0 mm. Viewed from a different perspective, the inner diameter and/or the length of the tip will be selected such that the syringe and tip can be inserted into the needleless connector at an angle (with respect to a hypothetical central axis extending through the barrel and the tip of the syringe and a hypothetical central axis longitudinally extending through the needleless connector) without the reversed internal blunt cannula contacting the inner surface of the tip. In some embodiments, such angle will be 5 degrees, or 7 degrees, or 10 degrees, or 12.5 degrees, or 15 degrees, or 20 degrees, or even higher. While not limiting to the inventive subject matter, contemplated syringes may have a fixed or a rotating (typically polymeric) lock portion.

Still further, it is contemplated that contemplated syringes will have a tip cap rubber surface contact area of equal or more than 2.4 mm$^2$, and more preferably equal or more than 4.8 mm$^2$. In still further contemplated embodiments, the syringe has a glide force of about 1 to about 30 N, about 1 to about 20 N, or about 1 to about 10 N. In other embodiments, the syringe has a break loose force of about 10 to about 30 N or about 15 to 25 N. Exemplary syringes are commercially available, for example, from Becton Dickinson under the brand name Hylok or LLEC (Luer Lock extended channel), which are commonly used for viscous materials such as dermal fillers.

In some embodiments, and particularly in those where the luer lock included a luer collar that is rotatable about the syringe tip and where the luer collar further has a tip cap, the inventors observed that removal of the tip cap from the luer collar could in some instances lead to a situation where attempts to remove the tip cap by twisting the tip cap off the collar also resulted in rotation of the luer collar, thus slowing down or rendering more difficult the removal of the tip cap. In this context, it should be appreciated that the syringe will include a prefilled medication that in most cases will be a sterile solution. Thus, to maintain sterility before use, the syringe and luer lock will be packaged in a sterile wrapper and further the contents of the syringe is further protected with a tip cap. Most typically, the tip cap will be attached to the luer collar via a thread or press fit to so removably retain the tip cap on the luer collar. When in use, the tip cap is first screwed or picked off the luer collar, and the syringe is then attached to a patient's intravenous line (e.g., via a needleless connector having a reversed internal blunt cannula) using the luer lock. Such quick and needleless attachment is especially desirable where the medication in the syringe is an emergency medication (e.g., succinylcholine, ephedrine, amiodarone, adenosine, epinephrine, atropine, methylprednisolone, metoprolol, diltiazem, or procainamide). As will be readily appreciated, any delay in administration of the medication may lead to loss of time that may adversely affect treatment outcome.

Figure 6:
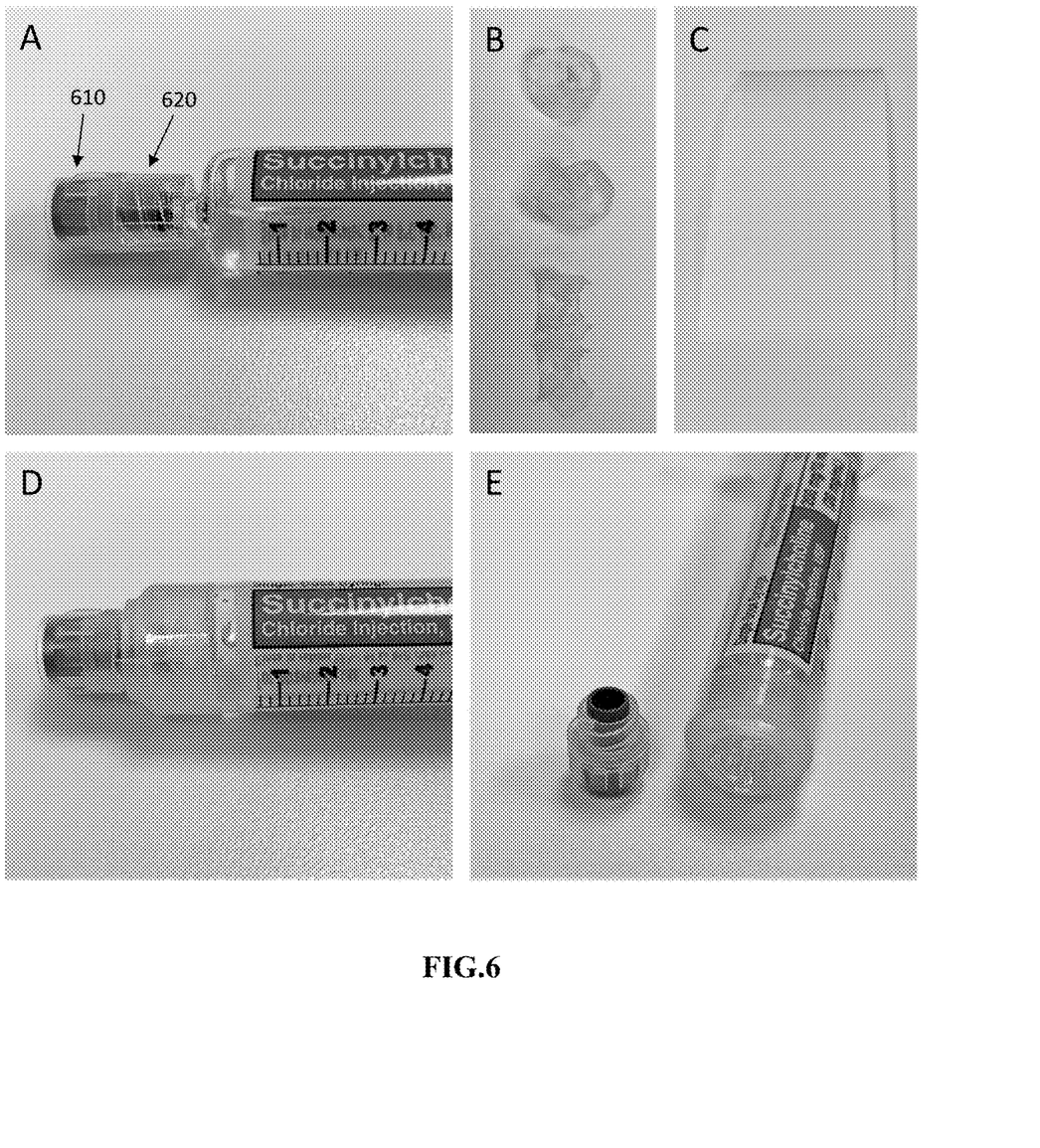
FIG. 6 depicts one exemplary lock restraint for a prefilled syringe. Panel (A) shows a prefilled syringe with a rotatable luer collar and tip cap; Panel (B) shows a restraint ring in open and closed configurations; Panel (C) shows an adhesive tape used in conjunction with the restraint ring; Panel (D) shows the restraint ring attached to the syringe and rotatable collar via the adhesive tape; and Panel (E) shows the syringe of Panel D with the tip cap removed.
Figure 7:
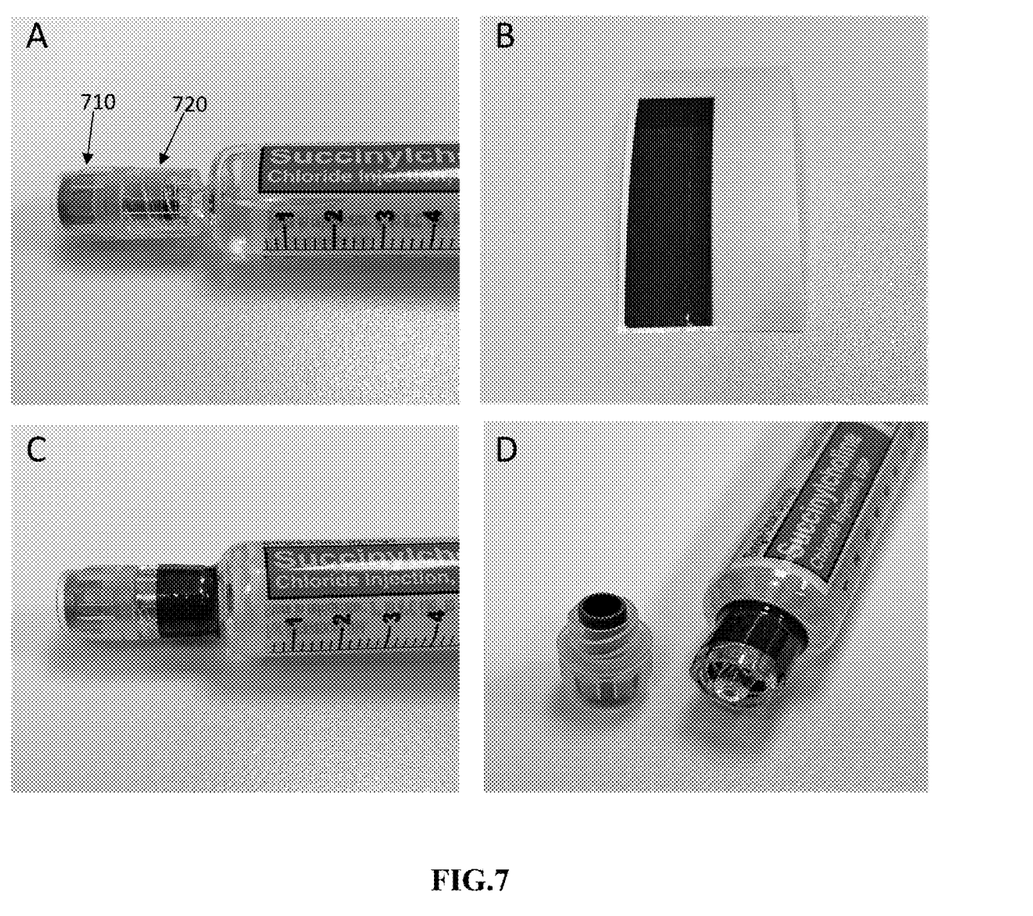
FIG. 7 depicts another exemplary lock restraint for a prefilled syringe. Panel (A) shows a prefilled syringe with a rotatable luer collar and tip cap; Panel (B) shows an adhesive tape used in conjunction with the rotatable luer collar; Panel (C) shows the rotatable luer collar attached to the syringe via the adhesive tape; and Panel (D) shows the syringe of Panel C with the tip cap removed.

To eliminate inadvertent motion of the luer collar during removal of the tip cap, the inventors have therefore devices systems and methods to at least temporarily immobilize the luer collar relative to the syringe barrel. To that end, a polymeric band was used to prevent rotation of the luer collar about the syringe tip when the tip cap is removed for the luer collar. As is shown in FIG. 6 and FIG. 7 more detail below, such band directly couple the syringe barrel to the luer collar or indirectly couple the syringe barrel to the luer collar via a restraint ring. Therefore, it should be appreciated that the tip cap can be removed while the luer collar remains, via the polymeric band, in a fixed position relative to the syringe tip, and that the polymeric band can be removed after removal of the tip cap or remain in place.

The panels of FIG. 6 depict one exemplary embodiment where the polymeric band is a plastic shrink wrap that indirectly couples the syringe barrel to the luer collar via a restraint ring. In Panel A, a syringe is shown with 10 mL capacity that is prefilled with a succinylcholine chloride formulation. A freely rotatable luer collar 620 is coupled to the syringe tip (preferably a tip as shown in FIGS. 3-4), and the distal end of the luer collar is sealed with a tip cap 610. The tip cap in this example is threaded and can be removed from the luer collar by twisting motion. However, it should be appreciated that the tip cap can also be removably coupled to the luer collar in various other manners, including press fit, a bayonet fit, etc. Panel B depicts an exemplary restraint ring, which is typically made of polycarbonate or other medically acceptable polymer and has grooves on its inner surface that are complementary to the grooves on the luer collar. Preferably, the restraining ring can be opened or separated in two or more portions for easy attachment and as is shown in Panel B. Thus, the two or more portions will be movable relative to each other. As will be readily appreciated, the exact shape and geometry of the restraining ring may vary, depending on the particular shape of the luer collar. In further preferred aspects, the outer diameter of the restraining ring has an outer diameter that is equal to that of the syringe barrel so that a clear adhesive band can be applied to further secure the restraining ring to the barrel.

While not limiting the inventive subject matter, it is typically preferred that the transparent adhesive band comprises a polypropylene or other polymeric film with a (typically but not necessarily) permanent acrylic adhesive as is exemplarily shown in Panel C. However, it should be noted that various alternative manners of coupling the restraining ring are also deemed suitable, including an adhesive on the restraining ring, or a press fit of restraining ring that snugly engages with the syringe barrel. Panel D exemplarily depicts the restraining ring coupled to the luer collar and affixed with the polymeric film (which may also be a shrink wrap film in addition to the adhesive or as a replacement for the adhesive). As can be readily seen from the example in Panel D, the luer collar is now fixedly coupled to the syringe tip with the tip cap being exposed and rotatably removable without inadvertent rotation of the luer collar. Panel E finally illustrates the syringe assembly with the tip cap removed and the thread of the tip cap exposed. Where desired, it should be appreciated that the connection between the restraining ring and the barrel can be frangible, and to such end a perforation or other manner of weakened connection may be provided in the polymeric band.

The panels of FIG. 7 depict another exemplary embodiment where the polymeric band is a plastic shrink wrap that directly couples the syringe barrel to the luer collar and in which a restraining ring is not needed. Here, in Panel A, a syringe is shown with 10 mL capacity that is prefilled with a succinylcholine chloride formulation. A freely rotatable luer collar 720 is coupled to the syringe tip (preferably a tip as shown in FIGS. 3-4), and the distal end of the luer collar is sealed with a tip cap 710. As in FIG. 6 above, the tip cap in this example is threaded and can be removed from the luer collar by twisting motion. Likewise, it should be appreciated that the tip cap can also be removably coupled to the luer collar in various other manners, including press fit, a bayonet fit, etc. Panel B depicts a polymeric band, typically with an adhesive that has a first and a second area, with first and second areas being of distinct color (here: first area is transparent/has no color and second are is dark blue). It is further contemplated that the polymeric band will be made of or comprise a shrink wrap polymer While not limiting the inventive subject matter, it is typically preferred that the transparent band may also comprise a (typically but not necessarily) permanent acrylic adhesive. Thus, it should be appreciated that the polymeric band can be used to directly couple the syringe barrel to the luer collar without an intermediary restraining ring.

Panel C exemplarily depicts the luer collar affixed to the syringe barrel by the polymeric film (which is preferably a shrink wrap film in addition to an optional adhesive). As can be readily seen from the example in Panel C, the luer collar is now fixedly coupled to the syringe tip with the tip cap being exposed and rotatably removable without inadvertent rotation of the luer collar. Panel D finally illustrates the syringe assembly with the tip cap removed and the thread of the tip cap exposed. Once more, and where desired, it should be appreciated that the connection between the luer collar ring and the barrel can be frangible, and to such end a perforation or other manner of weakened connection may be provided in the polymeric band. For example, the polymeric band may be made of or comprise a polyethylene terephthalate (PET) film wrap-type polymer film with a permanent acrylic adhesive that is applied around the luer collar and syringe barrel and that is then heat-shrunk onto the body of the syringe. Directed heat (~190° C.) is applied to the luer collar for 2-3 seconds which effectively shrinks the film firmly onto the syringe barrel and the luer collar, thereby immobilizing the luer collar. This solution also allows the luer lock to remain unhindered after tip cap removal and easily accessible for attachment to a port.

Regardless of the manner of coupling the luer collar to the barrel, it should be appreciated that the luer modifications of FIG. 6-7 are particularly suitable for the compositions, devices, and uses presented herein. Therefore, while all prefilled medications are deemed suitable for use herein (e.g., anesthetics, antibiotics, etc.), especially preferred medications are those used in emergency uses and crash carts where administration must be performed promptly and without interruption necessitated by clearing a clogged line, reconnecting a malfunctioning syringe, and/or preparing a new vascular access. Typical drugs for use with the syringes presented herein include those used in cardiac/vascular emergencies, pulmonary emergencies, anaphylaxis, etc. Consequently, suitable drugs include succinylcholine, ephedrine, amiodarone, adenosine, epinephrine, atropine, methylprednisolone, metoprolol, diltiazem, and procainamide. In most embodiments, the syringes will be prefilled with a volume of the drug, typically at a volume of at least 1 mL, or at least 5 mL, or at least 10 mL, or about 5 mL or about 10 mL. As will be readily appreciated, the emergency drug in such products will be present at a pharmaceutically effective concentration to treat any emergency condition. Suitable formulation types of the drug compositions include solutions with single, binary, or higher solvent systems, dispersed systems (e.g., preferably emulsions or suspensions). Moreover, and viewed from a different perspective, the medications will typically include ready-to-administer formulations that do not require any further modification (e.g., dilution, reconstitution, filter sterilization, etc.) before administration to an individual in need thereof.

Of course, it should also be appreciated that the prefilled syringe may be provided with an IV administration set or other bags or tubing that will most typically comprise at least one needleless connector that may or may not have a reversed internal blunt cannula. Still further, it should be noted that the prefilled syringe will typically be sterilized using terminal sterilization, e-beam or gamma ray radiation, ethylene oxide, etc.

Moreover, it should be recognized that contemplated prefilled glass syringes are especially advantageous for drug compositions that are sensitive to components that would otherwise leach from a plastic syringe (such as plasticizers, dyes, metals, etc.), particularly where the pH of the drug composition is in the acidic range (e.g., equal or less than 5.0, or equal or less than 4.5, or equal or less than 4.0, or equal or less than 3.5), where the drug is sensitive to oxygen ingress, or where the composition comprises a solvent that is incompatible with polymers used in plastic syringes such as polypropylene or polyethylene. Therefore, and viewed form a different perspective, contemplated systems and methods will also advantageously help improve chemical stability of otherwise relatively labile compounds (e.g., succinylcholine) under refrigeration conditions (about 2° C. to about 8° C., or about 5° C.) and at room temperature (about 25° C.).

For example, the stability of a succinylcholine composition in a glass syringe will typically be increased such that total impurities are equal or less than 12%, or equal or less than 10%, more typically equal or less than 8%, even more typically equal or less than 6%, or equal or less than 4%, or equal or less than 2% after storage at 2-8° C. for 12, 15, 18, or 24 months as determined HPLC as is described in more detail below. Thus, total impurities will preferably be in the range of between 1-3%, or between 2-5%, or between 4-8%, or between 5-10% after storage at 2-8° C. for 15 months as determined HPLC. Additionally, it is contemplated that after storage of a succinylcholine composition in a glass syringe at 2-8° C. for 12, 15, 18, or 24 months, no more than 8%, or no more than 6%, or no more than 4%, or no more than 2% of succinylmonocholine chloride (as primary degradation product) are present. Thus, succinylmonocholine chloride may be present after storage of a succinylcholine composition in a glass syringe at 2-8° C. for 12, 15, 18, or 24 months in a range of between 1-3%, or between 2-5%, or between 4-8%, or between 5-10%.

In further contemplated aspects, improved stability is also contemplated where the succinylcholine composition is stored in a glass syringe at about 25° C. For example, succinylmonocholine chloride may be present after storage of a succinylcholine composition in a glass syringe at about 25° C. for 14-60 days (or for 7-14 days, or for 14-21 days, or for 21-28 days, or for 28-40 days, or for 40-60 days) in a range of between 1-3%, or between 2-5%, or between 4-8%, or between 5-10%, particularly where the prefilled syringe was not previously subjected extended storage at 2-8° C. In such cases, for example where the previous refrigerated storage was between 1-3 months, the succinylmonocholine chloride may be present after subsequent storage about 25° C. for 14-60 days (or for 7-14 days, or for 14-21 days, or for 21-28 days, or for 28-40 days, or for 40-60 days) in a range of between 2-5%, or between 4-8%, or between 5-10%. Likewise, where the previous refrigerated storage was between 3-6 months, the succinylmonocholine chloride may be present after subsequent storage about 25° C. for 14-50 days (or for 7-14 days, or for 14-21 days, or for 21-28 days, or for 28-40 days, or for 40-50 days) in a range of between 3-6%, or between 5-9%, or between 8-12%, and where the previous refrigerated storage was between 6-15 months, the succinylmonocholine chloride may be present after subsequent storage about 25° C. for 14-40 days (or for 7-14 days, or for 14-21 days, or for 21-28 days, or for 28-40 days) in a range of between 3-7%, or between 5-10%, or between 8-12%.

In some embodiments, the drug composition comprises a drug for emergency medical administration, a tonicity agent, optionally one or more pH adjusting agents, and water.

In some embodiments, the drug for emergency medical administration is succinylcholine, selected from the group consisting of ephedrine, amiodarone, adenosine, epinephrine, atropine, methylprednisolone, metoprolol, diltiazem, and procainamide, and pharmaceutically acceptable salts thereof. In preferred embodiments, the drug for emergency medical administration is succinylcholine or a pharmaceutically acceptable salt thereof, and most preferably, succinylcholine chloride. In some embodiments, the drug for emergency medical administration is present in the composition in a therapeutically effective amount. In some embodiments, the drug for emergency medical administration is succinylcholine chloride and the succinylcholine chloride is present in the composition in an amount of about 10 to about 30 mg/mL, about 15 to about 25 mg/mL, or about 20 mg/mL.

In some embodiments, the tonicity agent is selected from the group consisting of dextrose, mannitol, potassium chloride, and sodium chloride. In preferred embodiments, the tonicity agent is sodium chloride. In some embodiments, the tonicity agent is present in the composition in an amount sufficient to provide an isotonic solution. In some embodiments, the tonicity agent is present in the composition in an amount sufficient to provide an osmolality of about 260 to about 340 mOsm/kg. In some embodiments, the tonicity agent is sodium chloride and the sodium chloride is present in the composition in an amount of about 4 to about 7 mg/mL, about 5 to about 6 mg/mL, about 5 mg/mL, or about 6 mg/mL.

In some embodiments, the pH adjusting agents are selected from the group consisting of acidifying agents, alkalizing agents, and buffering agents. In some embodiments, the pH adjusting agent is selected from the group consisting of citric acid, acetic acid, hydrochloric acid, sodium hydroxide, sodium citrate, potassium hydroxide, and potassium citrate. In preferred embodiments, pH adjusting agent is hydrochloric acid and/or sodium hydroxide. In some embodiments, the pH adjusting agent is present in the composition in an amount sufficient to provide a pH of about 3 to about 4.5, about 3 to about 4, about 3.5 to about 4.5, or about 3.5 to about 4, or about 3.6.

EXAMPLES

Example 1: Succinylcholine Composition

In one example, where the drug composition comprises succinylcholine, a 5 mL or 10 mL glass syringe (e.g., syringes with inner tip diameter of 1.7 mm) can be filled with a composition as shown in Table 1 where the composition has a pH of about 3.0 to about 4.5. Tonicity is adjusted to about 260 to about 340 mOsm/kg, and in preferred aspects, the succinylcholine chloride is present in the succinylcholine composition in an amount of about 20 mg/mL and the sodium chloride is present in the succinylcholine composition in an amount of about 5.50-6.00 mg/mL.

TABLE 1

| Ingredient | Grade | Function | Qty/mL |
|---|---|---|---|
| Succinylcholine Chloride | USP | Active ingredient | 20.0 mg |
| Sodium Chloride | USP | Tonicity agent | 5.56 mg |
| Hydrochloric Acid | NF | pH adjuster | q.s. for pH adjustment to about pH 3.6 |
| Sodium Hydroxide | NF | pH adjuster | q.s. for pH adjustment to about pH 3.6 |
| Water for Injection | USP | Vehicle | q.s. to 1.0 mL 5 ml per Syringe 10 ml per Syringe |

Example 2: Stability of a Succinylcholine Composition at 25° C.

Advantageously, thusly prefilled glass syringes afford relatively high stability and purity throughout extended periods of storage despite the acidic pH of the solution.

Three batches of the succinylcholine composition of Example 1 in a 5 mL Becton Dickinson LLEC glass syringe with inner tip diameter of 1.7 mm were prepared and stability was tested over 3 months of storage at 25° C. and 60% relative humidity. Content of succinylcholine chloride, impurities succinylmonocholine chloride, succinic acid, unidentified impurity 1, unidentified impurity 2, and total impurities were measured at 0, 1, 2, and 3 months by HPLC according to Example 4 below. Unidentified impurity 1 and unidentified impurity 2 are referenced in the USP monograph for impurity detection in succinylcholine, First Supplement to USP 39-NF 34. Appearance, pH, osmolality, and particulate content were also measured at 0, 1, 2, and 3 months. The results are included in Table 2 below.

As illustrated by Table 3 above, the succinylcholine composition in the glass syringe contained not more than about 2% total impurities after storage at 5° C. for 3 months as determined by HPLC. Likewise, with respect to degradation it was determined that the succinylcholine composi-

TABLE 2

| Month | Batch | Appearance* | pH | SCC | SMCC | SA | Impurity 1 | Impurity 2 | Total impurities | P ≥ 10 μm | P ≥ 25 μm | Osmolality (mOsm/kg) |
|---|---|---|---|---|---|---|---|---|---|---|---|---|
| 0 | 1 | complies | 3.9 | 99.3% | 0.5% | <LOQ | <LOQ | <LOQ | 0.5% | 34 | 0 | 314 |
| 0 | 2 | complies | 3.9 | 99.8% | 0.4% | ND | 0.2% | <LOQ | 0.4% | 25 | 0 | 313 |
| 0 | 3 | complies | 3.9 | 97.6% | 0.4% | ND | <LOQ | 0.2% | 0.4% | 65 | 1 | 312 |
| 1 | 1 | complies | 3.4 | 93.5% | 2.5% | 0.1% | 0.2% | ND | 2.7% | — | — | — |
| 1 | 2 | complies | 3.4 | 94.8% | 2.3% | 0.1% | <LOQ | 0.1% | 2.4% | — | — | — |
| 1 | 3 | complies | 3.4 | 94.5% | 2.2% | 0.1% | <LOQ | <LOQ | 2.3% | — | — | — |
| 2 | 1 | complies | 3.3 | 93.8% | 4.0% | 0.3% | 0.5% | 0.1% | 4.3% | — | — | — |
| 2 | 2 | complies | 3.3 | 93.8% | 3.9% | 0.3% | 0.3% | 0.3% | 4.2% | — | — | — |
| 2 | 3 | complies | 3.3 | 93.8% | 3.8% | 0.2% | 0.3% | 0.3% | 4.0% | — | — | — |
| 3 | 1 | complies | 3.3 | 91.6% | 4.9% | 0.4% | 0.2% | <LOQ | 5.4% | 75 | 1 | 316 |
| 3 | 2 | complies | 3.3 | 92.7% | 4.9% | 0.4% | 0.1% | <LOQ | 5.3% | 63 | 0 | 318 |
| 3 | 3 | complies | 3.3 | 92.6% | 4.8% | 0.4% | 0.1% | <LOQ | 5.2% | 133 | 0 | 316 |

ND = not detected;
*Clear, colorless solution essentially free of visible particles;
SCC: Succinylcholine chloride; SMCC: Succinylmonocholine chloride; SA: Succinic acid: P: Particle; >LOQ = that the amount detected is less than the limit of quantitation of the HPLC method.
— = not measured.

As illustrated by Table 2 above, the succinylcholine composition in the glass syringe contained not more than about 6% total impurities after storage at 25° C. for 3 months as determined by HPLC. Likewise, with respect to degradation it was determined that the succinylcholine composition in the glass syringe contained not more than about 4% succinylmonocholine chloride (as primary degradation product) after storage at 25° C. for 3 months as determined by HPLC, and that the succinylcholine composition in the glass syringe contained not more than about 1% succinic acid after storage at 25° C. for 3 months as determined by HPLC.

tion in the glass syringe contained not more than about 2% succinylmonocholine chloride (as primary degradation product) after storage at 5° C. for 3 months as determined by HPLC, and that the succinylcholine composition in the glass syringe contained not more than about 1% succinic acid after storage at 5° C. for 3 months as determined by HPLC.

Example 3: Stability of a Succinylcholine Composition at 5° C.

Stability of the three batches of Example 2 was also tested over 3 months of storage at 5° C. Content of succinylcholine chloride, impurities succinylmonocholine chloride, succinic acid, unidentified impurity 1, unidentified impurity 2, and total impurities were measured at 0 and 3 months by HPLC according to Example 4 below. Unidentified impurity 1 and unidentified impurity 2 are referenced in the USP monograph for impurity detection in succinylcholine, First Supplement to USP 39-NF 34. Appearance, pH, osmolality, and particulate content were also measured at 0 and 3 months. The results are included in Table 3 below.

Example 4: Analytic Protocols

In general, analytic protocols for succinylcholine are well known in the art, and the following TLC and HPLC protocols are suitable for use herein (which are based on the USP monographs):

Analytic Protocol (TLC):

Standard solution: 1 mg/mL of USP Succinylcholine Chloride RS in water; Sample solution: 1 mg/mL of succinylcholine chloride in water; Adsorbent: 0.25-mm layer of chromatographic silica gel with an application volume of 1 mcL. The plate is run with a developing solvent system that consists of acetone and 1 N hydrochloric acid (1:1). Analysis is performed by running standard and sample solution in parallel. Sample and standard spots are detected by heating the plate to 105° C. for 5 min, followed by cooling and spraying with potassium bismuth iodide test solution and subsequent heating to 105° C. for another 5 min.

TABLE 3

| Month | Batch | Appearance* | pH | SCC | SMCC | SA | Impurity 1 | Impurity 2 | Total impurities | P ≥ 10 μm | P ≥ 25 μm | Osmolality (mOsm/kg) |
|---|---|---|---|---|---|---|---|---|---|---|---|---|
| 0 | 1 | complies | 3.9 | 99.3% | 0.5% | <LOQ | <LOQ | <LOQ | 0.5% | 34 | 0 | 314 |
| 0 | 2 | complies | 3.9 | 99.8% | 0.4% | ND | 0.2% | <LOQ | 0.4% | 25 | 0 | 313 |
| 0 | 3 | complies | 3.9 | 97.6% | 0.4% | ND | <LOQ | 0.2% | 0.4% | 65 | 1 | 312 |
| 3 | 1 | complies | 3.7 | 98.3% | 1.1% | <LOQ | 0.2% | <LOQ | 1.1% | 66 | 0 | 310 |
| 3 | 2 | complies | 3.6 | 98.9% | 0.9% | <LOQ | 0.1% | <LOQ | 0.9% | 88 | 1 | 311 |
| 3 | 3 | complies | 3.7 | 99.3% | 0.9% | <LOQ | 0.1% | <LOQ | 0.9% | 63 | 0 | 310 |

ND = not detected;
*Clear, colorless solution essentially free of visible particles;
SCC: Succinylcholine chloride; SMCC: Succinylmonocholine chloride; SA: Succinic acid: P: Particle; >LOQ = that the amount detected is less than the limit of quantitation of the HPLC method.
— = not measured.

Analytic Protocol (HPLC) for Succinylcholine:

Mobile phase: Prepare a 1 in 10 solution of 1 N aqueous tetramethylammonium chloride in methanol. Adjust with hydrochloric acid to a pH of about 3.0.

Standard solution: 8.8 mg/mL of USP Succinylcholine. Succinylcholine Chloride Chloride RS prepared as follows. Transfer a suitable amount of USP Succinylcholine Chloride RS to a suitable volumetric flask and dissolve in 40% of the total volume of water. Dilute with Mobile phase to volume while mixing.

Sample solution: 8.8 mg/mL of Succinylcholine Chloride prepared as follows. Transfer a suitable amount of Succinylcholine Chloride to a suitable volumetric flask and dissolve in 40% of the total volume of water. Dilute with Mobile phase to volume while mixing.

Conventional HPLC system is operated using UV detection at 214 nm and a 4-mm×25-cm, 10 μm L3 packing (normal phase, silica) at a flow rate of 0.75 ml/min.

Analysis is performed on standard and sample solutions and percentage of succinylcholine chloride is calculated using the following equation: Result=$(r_U/r_S) \times (C_S/C_U) \times 100$, where $r_U$ is peak response from the sample solution, $r_S$ is peak response from the standard solution, $C_S$ is concentration of USP Succinylcholine Chloride RS in the standard solution (mg/mL), and $C_U$ is concentration of Succinylcholine Chloride in the sample solution (mg/mL).

Analytic Protocol (HPLC) for Impurities:

Buffer: 3.85 g/L of anhydrous sodium 1-pentanesulfonate, 2.9 g/L of sodium chloride, and 1% (v/v) of 1 N sulfuric acid in water.

Mobile phase: Acetonitrile and Buffer (5:95).

Standard solution: 0.05 mg/mL of USP Succinylmonocholine Chloride RS in Mobile phase.

Sample solution: Sample solution: 10 mg/mL of Succinylcholine Chloride in mobile phase.

Conventional HPLC system is operated using UV detection at 214 nm and a 4.6-mm×25-cm, L1 packing (octadecyl silane chemically bonded to porous silica or ceramic microparticles, 1.5 to 10 μm in diameter) at a flow rate of 0.75 ml/min.

Analysis is performed on standard and sample solutions and percentage of succinylcholine chloride is calculated using the following equation: Result=$(r_U/r_S) \times (C_S/C_U) \times (1/F) \times 100$, where $r_U$ is peak response from the sample solution, $r_S$ is peak response from the standard solution, $C_S$ is concentration of USP Succinylcholine Chloride RS in the standard solution (mg/mL), $C_U$ is concentration of Succinylcholine Chloride in the sample solution (mg/mL), and F is the relative response factor.

Example 5: Syringe Parameters

Break loose force and glide force were also measured in quintuplicate at each time point in Examples 2 and 3 above. The results are included in Table 4 below:

TABLE 4

| Month | Temperature | Batch | Break Loose Force (Newtons) | Glide Force (Newtons) |
|---|---|---|---|---|
| 0 | 25° C. | 1 | 16, 16, 16, 16, 13 | 6, 24, 6, 20, 5 |
| 0 | 25° C. | 2 | 13, 16, 14, 18, 15 | 5, 11, 6, 7, 11 |
| 0 | 25° C. | 3 | 16, 14, 18, 18, 24 | 14, 13, 9, 6, 7 |
| 1 | 25° C. | 1 | 16, 19, 21, 18, 16 | 6, 6, 21, 17, 12 |
| 1 | 25° C. | 2 | 19, 17, 13, 16, 17 | 28, 6, 8, 9, 6 |
| 1 | 25° C. | 3 | 18, 21, 15, 15, 21 | 8, 23, 16, 12, 7 |
| 2 | 25° C. | 1 | 20, 18, 19, 17, 22 | 5, 6, 7, 4, 6 |
| 2 | 25° C. | 2 | 23, 19, 16, 19, 17 | 5, 10, 6, 5, 6 |
| 2 | 25° C. | 3 | 16, 18, 16, 21, 21 | 9, 6, 8, 11, 10 |
| 3 | 25° C. | 1 | 22, 19, 19, 19, 18 | 9, 12, 8, 8, 6, 9 |
| 3 | 25° C. | 2 | 15, 19, 18, 22, 19 | 6, 7, 16, 13, 8 |
| 3 | 25° C. | 3 | 25, 25, 22, 14, 17 | 6, 9, 6, 6, 6 |
| 3 | 5° C. | 1 | 23, 16, 19, 20, 18 | 23, 7, 6, 33, 7 |
| 3 | 5° C. | 2 | 20, 17, 20, 22, 10 | 9, 6, 18, 7, 6 |
| 3 | 5° C. | 3 | 15, 17, 18, 16, 20 | 9, 26, 6, 7, 8 |

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.).

In some embodiments, the drug composition in the prefilled syringe is administered to a patient via the patient's intravenous line. In some embodiments, the drug composition in the prefilled syringe is administered to the patient by reversibly attaching the syringe to the patient's intravenous line via the Luer-lock, delivering the drug composition from the syringe into the patient's intravenous line, and administering the drug composition from the patient's intravenous line to the patient. The succinylcholine drug composition is typically administered to the patient at a rate sufficient to cause the desired skeletal muscle relaxation. In some embodiments, the succinylcholine drug composition is administered to the patient at a rate of about 0.5 to about 10 mg per minute or about 2 to about 5 mg per minute, or about 2.5 to about 4.3 mg per minute. In some embodiments, the succinylcholine drug composition is administered to the patient in an amount of about 0.01 to about 3 mg/kg, about 0.04 to about 0.07 mg/kg, about 0.3 to about 1.1 mg/kg, about 0.6 mg/kg, 1 mg/kg, or 2 mg/kg.

In some embodiments, the present invention encompasses a method for providing skeletal relaxation comprising administering the succinylcholine drug composition in a prefilled syringe to a patient in need thereof via the patient's intravenous line. In some embodiments, the succinylcholine drug composition is administered as an adjunct to general anesthesia, to facilitate tracheal intubation, or to provide skeletal muscle relaxation during surgery or mechanical ventilation.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. The term "about" where used in conjunction of a numeric value refers to a range of +/−10% of that numeric value, inclusive. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A prefilled syringe, comprising:
   a syringe barrel containing a ready-to-administer medication, wherein the barrel is fluidly coupled to a syringe tip;
   a luer-lock coupled to the syringe to allow reversible attachment of the syringe to a needleless connector having a reversed internal blunt cannula;
   wherein the luer-lock comprises a luer collar that is rotatable about the syringe tip;
   a tip cap rotatably coupled to and removable from the luer collar; and
   a polymeric band coupled to the syringe to prevent rotation of the luer collar about the syringe tip when the tip cap is removed from the luer collar,
   wherein the medication is a succinylcholine composition, and
   wherein the succinylcholine composition, when disposed in a glass syringe, contains not more than about 6% total impurities after storage at 2-8° C. for 15 months, followed by storage at about 25° C. for 14 days as determined by high performance liquid chromatography.

2. The prefilled syringe of claim 1 wherein the polymeric band directly couples the syringe barrel to the luer collar.

3. The prefilled syringe of claim 1 wherein the polymeric band indirectly couples the syringe barrel to the luer collar via a restraint ring.

4. The prefilled syringe of claim 3 wherein the restraint ring comprises a first and a second portion that can be moved relative to each other.

5. The prefilled syringe of claim 1 wherein the polymeric band comprises a shrink wrap polymer.

6. The prefilled syringe of claim 1 wherein the polymeric band comprises an adhesive.

7. The prefilled syringe of claim 1 wherein the syringe is a glass syringe.

8. The prefilled syringe of claim 1 wherein the syringe tip has in internal channel having a diameter of between 1.2-2.2 mm.

9. The prefilled syringe of claim 1 wherein the syringe tip has in internal channel having a diameter of at least 1.5 mm.

10. The prefilled syringe of claim 1 wherein the syringe tip has in internal channel having a diameter of about 1.7 mm.

11. The prefilled syringe of claim 1, wherein the succinylcholine composition has a pH of about 3.0 to about 4.5.

12. A prefilled glass syringe, comprising:
    a glass syringe having a barrel containing a ready-to-administer medication, wherein the barrel is fluidly coupled to a syringe tip;
    a luer-lock coupled to the syringe to allow reversible attachment of the syringe to a needleless connector having a reversed internal blunt cannula;
    wherein the luer-lock comprises a luer collar that is rotatable about the syringe tip;
    a tip cap rotatably coupled to and removable from the luer collar;
    a polymeric band coupled to the syringe to prevent rotation of the luer collar about the syringe tip when the tip cap is removed for the luer collar;
    wherein the syringe tip has an internal channel that has a diameter of 1.2-2.2 mm inner diameter;
    wherein the diameter of the internal channel and/or a length of the syringe tip is configured such that the syringe tip can be inserted into the needleless connector at an angle with respect to a hypothetical central axis extending through the barrel and the tip of the syringe and a hypothetical central axis longitudinally extending through the needleless connector without the reversed internal blunt cannula contacting the inner surface of the tip;
    wherein the medication is a succinylcholine composition; and
    wherein the succinylcholine composition disposed in the glass syringe contains not more than about 6% total impurities after storage at 2-8° C. for 12 months, followed by storage at about 25° C. for 14 days as determined by high performance liquid chromatography.

13. The prefilled glass syringe of claim 12 wherein the internal channel has a diameter of about 1.7 mm, and wherein the prefilled glass syringe contains 5 mL or 10 mL of the succinylcholine composition.

14. The prefilled glass syringe of claim 12, wherein the succinylcholine composition has a pH between 3-4.

* * * * *